(12) United States Patent
Hall et al.

(10) Patent No.: US 7,744,863 B1
(45) Date of Patent: Jun. 29, 2010

(54) METHOD OF INDUCING IMMUNE TOLERANCE

(76) Inventors: Bruce Milne Hall, 14 Vernon Street, Strathfield (AU) 2135; Suzanne Jean Hodgkinson, 14 Vernon Street, Strathfield (AU) 2135

( * ) Notice: Subject to any disclaimer, the term of this patent is extended or adjusted under 35 U.S.C. 154(b) by 1534 days.

(21) Appl. No.: 10/148,010

(22) PCT Filed: Nov. 24, 2000

(86) PCT No.: PCT/AU00/01441

§ 371 (c)(1),
(2), (4) Date: Mar. 10, 2003

(87) PCT Pub. No.: WO01/37860

PCT Pub. Date: May 31, 2001

(30) Foreign Application Priority Data

Nov. 26, 1999 (AU) .................................. PQ4312

(51) Int. Cl.
*A61K 38/20* (2006.01)
(52) U.S. Cl. .................. 424/85.2; 424/154.1; 424/156.1
(58) Field of Classification Search ........................ None
See application file for complete search history.

(56) References Cited

FOREIGN PATENT DOCUMENTS

WO   WO 94/28027   12/1994
WO   WO 98/47531   10/1998

OTHER PUBLICATIONS

Auchincloss, "Transplantation Immunology", Bach and Auchincloss, Eds.,. Wiley-Liss, New York, 1995; Chapter 11, pp. 211-218.*
Schroeder et al., J. Surg. Res. 2003, 111:109-119.*
Chatenoud et al., J Immunol. Mar. 15, 1997;158(6):2947-54.*
Chatenoud et al., Curr Opin Immunol. Dec. 2005;17(6):632-7.*
He et al., Journal of the American Society of Nephrology, Sep. 1999, vol. 10, p. 703A.*
Lopez et al., J Exp Med. Jan. 1, 1988;167(1):219-24.*
Tang et al., J Exp Med. Jun. 7, 2004;199(11):1455-65.*
Harley et al., Curr Opin Immunol. Dec. 1998;10(6):690-6.*
Donald Leung, J Allergy Clin Immunol. May 2000;105(5):860-76.*
Yawalkar et al., J Allergy Clin Immunol. Dec. 2000;106(6):1171-6.*
Umland et al., J Immunol. Mar. 1, 1989;142(5):1528-35.*
Sherer et al., Lupus. 2000;9(1):42-6.*
Graber et al., J Biol Chem. Jun. 30, 1995;270(26):15762-9.*
Plugariu et al., Biochemistry. Dec. 5, 2000;39(48):14939-49.*
Whitty et al., Chem. Biol. Apr. 1999;6(4):R107-18.*
Williamson et al., J Clin Pathol. Sep. 1985;38(9):1007-12.*
Nagano et al., J Clin Immunol. Nov. 1999;19(6):422-7.*
Assein et al., "Stable Polarization of Peripheral Blood T Cells Towards Type 1 or Type 2 Phenotype After Polyclonal Activation" European Journal of Immunology 28:532-539 (1998).
De Carli et al., "Immortalization with Herpesvirus Saimiri Modulates the Cytokine Secretion Profile of Established Th1 and Th2 Human T Cell Clones" Journal of Immunology 151:5022-5030 (1993).
Flamand et al., "Anti-CD3 Antibodies Induce T Cells from Unprimed Animals to Secrete IL-4 Both InVitro and In Vivo" Journal of Immunology 144(8):2875-2882 (1990).
Hongwei et al., "Eosinophils in Acute Renal Allograft Rejection" Transplant Immunology 2(1):41-46 (1994).
Martinez et al., "Evidence for a Nonclassical Pathway of Graft Rejection Involving Interleukin 5 and Eosinophils" Transplantation 55(4):909-918 (1993).
Nicola (Ed.) "Interleukin-5 (IL-5)" In *Guidebook to Cytokines and Their Receptors* pp. 49-52 (1997).
Palmer and van Seventer, "Human T Helper Cell Differentiation Is Regulated by the Combined Action of Cytokines and Accessory Cell-Dependent Costimulatory Signals" J. of Immunology 158:2654-2662 (1997).
Piccinni et al., "Progesterone Favors the Development of Human T Helper Cells Producing Th2-type Cytokines and Promotes Both IL-4 Production and Membrane CD30 Expression in Established Th1 Cell Clones" Journal of Immunology 155:128-133 (1995).
Plain et al., "Induction of Specific Tolerance to Allografts in Rats by Therapy with Non-Mitogenic, Non-Depleting Anti-CD3 Monoclonal Antibody" Transplantation 67(4):605-613 (1999).
Posselt et al., "Induction of Donor-Specific Unresponsiveness by Intrathymic Islet Transplantation" Science 249:1293-1295 (1990).
Remuzzi et al., "Kidney Graft Survival in Rats Without Immunosuppressants After Intrathymic Glomerular Transplantation" Lancet 337:750-752 (1991).
Semnani et al., "Acquisition of Interleukin-5 Secretion by Human Naïve T-Helper Cells Is Regulated by Distinct Signals from Both the T-Cell Receptor/CD3 Complex and CD2" Scandinavian Journal of Immunology 47:436-443 (1998).
Kobayasi et al., J. Gastroenterol. (1998) 33:602-603.
Lin et al., Scand. J. Immunol. (1995) 4294):466-472.
Supplementary Partial European Search Report, for European patent application No. 00977328.4, 3 pages, 2003.

\* cited by examiner

*Primary Examiner*—Zachary Skelding
(74) *Attorney, Agent, or Firm*—Morrison & Foerster LLP

(57) ABSTRACT

A method of inhibiting Th1 immune response in a subject in need of such treatment which comprises administering to the subject effective amounts for inhibiting Th1 immune response of an anti-CD3 monoclonal antibody and IL-5 or an analogue or mimetic thereof.

5 Claims, 7 Drawing Sheets

METHOD OF INDUCING IMMUNE TOLERANCE

This application claims priority to PCT application PCT/AU00/01441 filed Nov. 24, 2000, which claims priority to Australian Application No. PQ4312/99, filed Nov. 26, 1999.

FIELD OF THE INVENTION

The present invention relates to methods and compositions for treating autoimmune disease and for inducing immune tolerance to transplants. In particular, but not exclusively, the present invention relates to induction of immune tolerance by inhibition of Th1 cell activity.

BACKGROUND OF THE INVENTION

The number of organ transplants performed in the United States is approximately 19,000 annually and consists predominantly of kidney transplants (11,000), liver transplants (3,600), heart transplants (2,300), and smaller numbers of pancreas, lung, heart-lung and intestinal transplants. Since 1989 when the United Network for Organ Sharing began keeping national statistics, approximately 190,000 organ transplants have been performed in the United States. A large but difficult to ascertain number of transplants were performed in the United States prior to 1989 and a similarly large number of transplants are performed in Europe and Australia and a smaller number in Asia.

Transplant tolerance remains an elusive goal for patients and physicians whose ideal would be to see a successful, allogeneic organ transplant performed without the need for indefinite, non-specific maintenance immunosuppressive drugs and their attendant, side effects. Over the past 10 years the majority of these patients have been treated with cyclosporin, azathioprine, and prednisone with a variety of other immunosuppressive agents being used as well for either induction or maintenance immunosuppression. The average annual cost per patient of maintenance immunosuppressive therapy in the United States is approximately $30,000. While the efficacy of these agents in preventing rejection is good, the side effects of immunosuppressive therapy are considerable because the unresponsiveness which they induce is nonspecific. For example, recipients can become very susceptible to infection and malignancy. Most known immunosuppressive therapies serve only to delay graft rejection and never lead to tolerance induction (12, 24) in "high responder" individuals, although some tolerance in "low responder" individuals has been reported (25, 26). A major goal in transplant immunobiology is the development of specific immune tolerance to organ transplants with the potential of freeing patients from the side effects of continuous pharmacological immunosuppression and its related complications and costs. Immune tolerance would also be of clinical significance in treatment of autoimmune diseases. In this sense immune tolerance is intended to mean the specific loss of lymphocyte reactivity to the antigen (eg. a donor allo- or xeno-antigen or an autoantigen). Although not necessarily correlating to an in vivo tolerance an in vitro analysis may be conducted as an indicator of in vivo tolerance.

Anti-T cell therapy (anti-lymphocyte globulin) has been used in rodents in conjunction with thymic injection of donor cells (Posselt et al. *Science* 1990; 249: 1293-1295 and Remuzzi et al. Lancet 1991; 337: 750-752). Thymic tolerance has proved successful in rodent models and involves the exposure of the recipient thymus gland to donor alloantigen prior to an organ allograft from the same donor. However, thymic tolerance has never been reported in large animals, and its relevance to tolerance in humans is unknown.

One approach to try to achieve such immunosuppression has been to expose the recipient to cells from the donor prior to the transplant, with the hope of inducing tolerance to a later transplant. This approach has involved placement of donor cells (e.g. bone marrow) presenting MHC Class 1 antigens in the recipient's thymus shortly after application of anti-lymphocyte serum (ALS) or radiation. However, this approach has proved difficult to adapt to live primates (e.g. monkeys; humans). ALS and/or radiation render the host susceptible to disease or side-effects and/or are insufficiently effective.

Autoimmune diseases represent a major public health problem. The autoimmune disease, type I diabetes is mediated by $CD8^+$ T cells mediated injury to the beta cells of the pancreas, multiple sclerosis is probably mediated by both $CD4^+$ T cells and $CD8^+$ T cells and rheumatoid arthritis is a immune inflammatory disease in which $CD4^+$ T cells play a central role. Glomerulonephritis is dependent upon $CD4^+$ T cell activation and mediated by $CD8^+$ T cells, which in experimental models can be regulated by suppressor T cells. Other auto-immune diseases affect a smaller proportion of patients but carry a significant disease burden and include myasthenia gravis, chronic inflammatory demyelinating neuropathy, inflammatory bowel disease, chronic active hepatitis, interstitial pneumonitis, dermatomyositis and systemic lupus erythematosis. The incidence of multiple sclerosis in the Western world is up to 60/100,000, total patients 3.6 million. Type I diabetes affects 0.25% of young people (30 million affected, 1.5 million new patients per year). Rheumatoid arthritis affects approximately 1% of the population or 6 million people in Western countries. Current therapies only aim to control disease activity by suppressing inflammation. Regular immunosuppressive drugs such as prednisone, azathioprine and cyclophosphamide will control diseases such as nephritis but do not always induce tolerance. More recently, newer immunosuppressive drugs have been used with some effect, including cyclosporine, FK506 and mycophenolate mofetil. In multiple sclerosis beta interferon and cepaxone a copolymer will reduce relapse rates but do not restore tolerance. Still further autoimmune diseases include asthma and the dermatological diseases psoriasis and atopic dermatitis.

T cell derived cytokines are thought to be mediators of induction and maintenance of immune mediated tolerance, but the precise cytokines involved are not known. The primary effectors of rejection are Th1 cells producing IL-2, IFN-$\gamma$, and TNF-$\alpha$, whilst Th2 cells producing IL-4, IL-10 have been implicated as regulator cells that inhibit Th1 cells and facilitate induction of tolerance (1-3). IL-4 and IL-10 have been extensively studied and have been reported to either accelerate rejection or prolong graft survival (4-9). IL-5 is an inducible glycoprotein cytokine produced mainly by activated T cells in response to antigenic or allergic stimulation. IL-5 promotes eosinophil and basophil growth, is a major inflammatory mediator in asthma and other allergic diseases and has a role in defence against parasitic infection (10). Its predominant effect is on eosinophil and basophil activation and proliferation. IL-5 also acts on B cells facilitating IgG isotype switching to $IgG_1$ and IgE (10). IL-5 acts on target cells through interaction with a specific IL-5 receptor composed of an IL-5 ligand binding alpha-subunit and a non-ligand binding beta-subunit that is shared by the receptors for IL-3 and GM-CSF. Expression of IL-5 receptors is restricted to eosinophils and basophils. IL-5 has no known direct effect on T cells, which lack the alpha receptor for IL-5 (10).

A reliable and safe approach to immunologic tolerance would be of tremendous value and appeal to autoimmune disease and transplant recipient patients and their physicians. Such an approach would have immediate application to autoimmune disease treatment and to treatment of patients with new organ transplants. There is also potential application to patients with existing transplants, with stable transplant function.

SUMMARY OF THE INVENTION

Accordingly, in a first aspect of the present invention there is provided a method of inhibiting Th1 immune response in a subject in need of such treatment which comprises administering to the subject effective amounts for inhibiting Th1 immune response of an anti-CD3 monoclonal antibody and IL-5 or an analogue or mimetic thereof.

In a second aspect of the present invention there is provided a method of inducing immune tolerance in a subject in need of such treatment which comprises administering to the subject effective amounts for inducing immune tolerance of an anti-CD3 monoclonal antibody and IL-5 or an analogue or mimetic thereof.

In a third aspect of the present invention there is provided a method of inducing graft immune tolerance in a transplant recipient subject which comprises administering to the subject effective amounts for inducing graft immune tolerance of an anti-CD3 monoclonal antibody and IL-5 or an analogue or mimetic thereof.

In a fourth aspect of the present invention there is provided a pharmaceutical composition comprising an anti-CD3 monoclonal antibody and IL-5 or an analogue or mimetic thereof in association with one or more suitable carriers and/or excipients.

In a fifth aspect of the present invention there is provided a veterinary composition comprising an anti-CD3 monoclonal antibody and IL-5 or an analogue or mimetic thereof in association with one or more suitable carriers and/or excipients.

In a sixth aspect of the present invention there is provided use of an anti-CD3 monoclonal antibody and IL-5 or an analogue or mimetic thereof in preparation of a composition for inhibiting Th1 immune response in a subject in need of such treatment.

In a seventh aspect of the present invention there is provided use of an anti-CD3 monoclonal antibody and IL-5 or an analogue or mimetic thereof in preparation of a composition for inducing immune tolerance in a subject in need of such treatment.

In an eighth aspect of the present invention there is provided use of an anti-CD3 monoclonal antibody and IL-5 or an analogue or mimetic thereof in preparation of a composition for treatment of autoimmune disease in a subject in need of such treatment.

In a ninth aspect of the present invention there is provided use of an anti-CD3 monoclonal antibody and IL-5 or an analogue or mimetic thereof in preparation of a composition for inducing graft immune tolerance in a transplant recipient subject.

In a tenth aspect of the present invention there is provided a kit for inhibiting Th1 immune response in a subject which comprises an anti-CD3 monoclonal antibody and IL-5 or an analogue or mimetic thereof.

Preferably the anti-CD3 monoclonal antibody is unable to bind to Fc receptors.

Preferably the subject is a mammal, particularly preferably the subject is a human.

Preferably the antibody is a humanised anti-CD3 monoclonal antibody.

In another preferred aspect of the invention the IL-5 is recombinant human IL-5.

Methods according to the present invention may be used for treatment of subjects suffering from or prone to suffer from an autoimmune disease. For example, the autoimmune disease may be type 1 diabetes, multiple sclerosis, rheumatoid arthritis, asthma, psoriasis, atopic dermatitis, glomerulonephritis, myasthenia gravis, chronic inflammatory demyelinating neuropathy, inflammatory bowel disease, chronic active hepatitis, interstitial pneumonitis, dermatomyositis or systemic lupus erythematosis.

Methods according to the invention may also be utilised for treatment of transplant recipients. The transplant may be an allotransplant or a xenotransplant. For example, the tissue transplanted may be kidney, liver, heart, lung, skin, pancreas, eye, cornea, bone marrow, muscle, connective tissue, vascular tissue, gastrointestinal tissue, nervous tissue or bone.

Anti-CD3 antibodies may be readily obtained or prepared by those skilled in the art. Examples of anti-CD3 antibodies are described in WO 91/01752, WO 93/19196, GB 2,268,744, WO 98/39363, WO 96/32137 and U.S. Pat. No. 5,335,573.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

All literature and patent documents cited in this specification are incorporated herein in their entirety by way of reference. The reference to any prior art in this specification is not, and should not be taken as, an acknowledgment or any form of suggestion that that prior art forms part of the common general knowledge in Australia.

BRIEF DESCRIPTION OF THE FIGURES

The present invention will be further described, by way of example only, with reference to the following figures.

Figure 1:
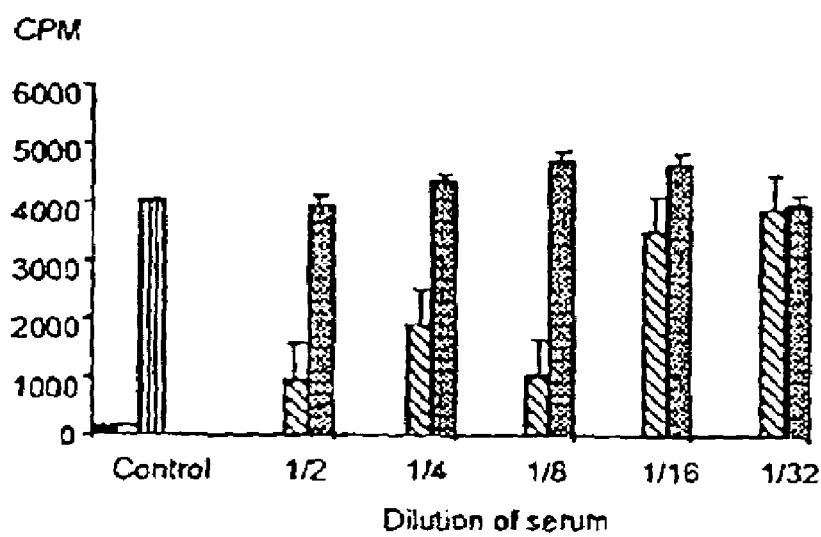
FIG. 1
Figure 1:
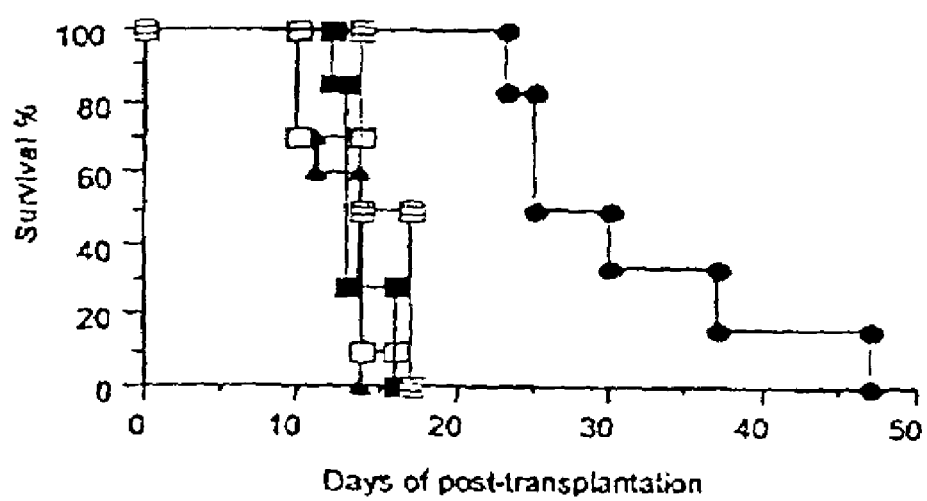

Shows the Effect of IL-5/Anti-IL-5 mAb on B13 Cell Lines and Allografts a. Proliferation of B13 was supported by 100 units of rIL-5 (▊), but not control supernatant (□) or media alone (■), and was inhibited by an eight fold dilutions of sera from DA rats 10 days after administration of 2 mg of anti-IL-5 mAb (▨), but not sera from DA rats give an isotype control A6 mAb (▊).

b. Effect of treatment with 4000 units of rIL-5 daily for 10 days post-transplantation prolonged fully allogeneic PVG neonatal cardiac allograft survival in DA rats (n=6/group) (—●—)($p<0.001$) compared to untreated controls —▲—and those treated with control supernatant (-□-), both anti-IL-5 mAb and rIL-5 (—■—) or anti-IL-5 mAb alone (—▣—).

FIG. 2.

Shows the Effect of rIL-5 on Fully Allogeneic Cardiac Graft Survival in Hosts Treated with Anti-T Cell mAb that Alone Cannot Induce Tolerance.

a. Neonatal PVG cardiac allografts in DA rats treated with anti-CD4 mAb therapy combined with rIL-5 (—□—) survived longer than rIL-5 therapy alone (—●—) or anti-CD4 mAb alone (—▲—)($p<0.001$) but comparable to syngeneic controls (—○—), which fail for non-immunological reasons in <100 days, /group).

b. Survival of fully allogeneic heterotopic PVG adult heart graft survival in high responder Lewis rats; rIL-5 combined with anti-CD3 mAb therapy prolonged survival (—□—)(n=16) compared to anti-CD3 mAb therapy alone (—△—)(n=10) ($p<0.028$), rIL-5 treatment (—●—) and untreated (—▲—). rIL-4 therapy combined with anti-CD3 mAb accelerated rejection (—■—) ($p<0.03$), compared to anti-CD3 mAb alone.

FIG. 3.

Shows Semi-Quantitative RT-PCR of mRNA from Th1 and Th2 Cytokines in Neonatal Heart Graft Recipients, Comparison of Normal Rejection and rIL-5 Treatment Groups.

a. Representative samples front syngeneic and allogeneic grafts given no treatment, or treated with rIL-5, rIL-5 plus anti-rIL-5 mAb, rIL-5 plus rIL-2 treatment. The earlier the cycle that product appears the greater the amount of the relevant mRNA. Duplicate reactions were performed at each cycle.

b. Semi-quantitative RT-PCR data expressed as median' cycle±range for each group (n=6). Groups analysed included DA syngeneic grafts (■); allogeneic grafts untreated (□); and treated with rIL-5 (▣); rIL-5 combined with anti IL-5 mAb (□); or rIL-5 combined with rIL-2 (□). Untreated controls had significantly increased mRNA for all cytokines compared to that in syngeneic grafts. rIL-5 treated had significantly reduced IL-2 in regional node ($p<0.0001$) and donor heart ($p<0.001$), as well as IFN-γ in lymph node. ($p<0.01$) compared to all other allograft groups, but these levels were not different to those in syngeneic grafts.

FIG. 4.

Shows the Effect of Co-Administration of Other Cytokines or mAb that Block Other Cytokines on the Ability of rIL-5 to Prolong Neonatal Allograft Survival.

a. Co-administration of rIL-5 and rIL-2 (—□—) prevented the prolongation of graft survival induced by rIL-5 (—●—) alone. Other groups include untreated (—▲—) and treated with IL-2 alone (—■—) or control supernatant (—△—); (n=6/group).

b. rIL-4 therapy alone (—□—) delayed graft rejection, but when combined with rIL-5 (—○—) grafts were rejected earlier than treatment with either cytokine alone ($p<0.05$). Other groups include untreated (—▲—) and rIL-5 treated (—●—).

c. Co-administration of the mouse anti-rat IL-4 mAb (MRC 0×81) with rIL-5 (—□—) had no effect on the delay in graft rejection induced by rIL-5 (—●—). Other groups include anti-IL-4 mAb alone (—■—) and isotype matched control (A6) mAb (—△—).

FIG. 5

Assessment of proteinuria (A) and serum anti-RTA Ab (B) in rats treated with G4.18 from 0-5 weeks (■) or 7-12 weeks (●), compared to HN positive (▲) and CFA negative (□) controls. A. Proteinuria expressed as mg/day (mean±SEM, n=5/group) was analysed at 2 weeks intervals from 4-12 weeks post-immunisation. The early G4.18 therapy group had less proteinuria at 10 ($p=0.0012$) and 12 weeks ($p=0.0598$) than HN controls and late (7-12 weeks) treatment groups. Early G4.18 treatment proteinuria was not different than CFA controls at all time points.

B. Serum anti-RTA Ab levels indicated as % binding of known positive (mean±SEM, n=5/group) were analysed at 2 weeks intervals from 4-12 weeks post-immunisation. Anti-RTA RTA Abs detected at 4 and 6 weeks were significantly higher titres in HN controls, and late G4.18 treatment groups compared to early G4.18 group ($p=0.002$ and $p<0.0001$, respectively). At 6 weeks and later all groups had similar anti-RTA ab.

The effect of rIL-5 on development of proteinuria in active Heymann nephritis. Lewis male rats were immunized with 15 mg of renal tubular antigen (RTA) emulsified in complete Freund's adjuvant containing heat killed mycobacteria tuberculosis H37 RA (Difco Bacto), as described (Penny, M. J., Boyd, R. A., Hall, B. M. Glomerular injury in active Heymann's nephritis is mediated by $CD8^+$ cells. J. Exp. Med. 188; 1775-1784. 1998). Disease activity was monitored by measurement of antibodies to RTA every 4 weeks, renal biopsies for IgG and complement deposition in glomeruli and 24 hour urine protein levels. Treatment with rIL-5 40,000 units per day ip for 10 days, commencing at 4 weeks after immunization. This is at a time prior to onset of proteinuria when the $CD8^+$ T cell response that mediates injury is developing but after the development of anti-RTA antibodies and their deposition in glomeruli. The rIL-5 markedly reduced proteinuria below that in untreated controls or controls treated with supernatant from non-transfected CHO-K1 cells. It did not totally abolish the proteinuria but was as effective as anti-CD3 therapy. rIL-5 therapy had no effect on the anti-RTA antibody response or on the deposition of IgG or complement in glomeruli. It did reduce the $CD8^+$ T cell and macrophage infiltrate in the glomeruli. Further it reduced the induction of Th1 cytokines.

FIG. 7

Effect of rIL-5 and anti-CD3 (G4.18) treatment of experimental allergic neuritis in Lewis male rats. Assessed by clinical score 0=no disease; +limp tail; ++weak hind limbs; +++paralysed hind limbs, ++++paralysed hind and fore limbs; ++++dead. Lewis rats were immunized with 0.25 mg bovine peripheral nerve myelin (P2) prepared as described (Kadlubowski M., Hughes, R. A. C., Gregson, N. A. J. Neurochem. 1984 42 123) emulsified with Freund's Complete Adjuvant (Sigma, St. Louis Mo.) with heat killed mycobacteria tuberculosis H37 RA (Difco Bacto). This lead to onset of disease with early clinical symptoms evident by day 11, and all animals develop disease. On day 12 when over 80% on animals have clinical disease treatments were started. These included G4.18 (3.5 mg/Kg/day ip for 10 days), rIL-5 5000 units ip per day daily for either 9 or 12 days, a combination of G4.18 and rIL-5 at the same dose. Controls included CHO-K1 supernatant from non transfected cell lines as a control for rIL-5 and untreated. In other experiments control isotype mAb BCLA8 was used and the disease course was identical to untreated controls. G4.18 alone had a more rapid effect than rIL-5 alone, but had a large relapse. Combined G4.18 was associated with a more rapid and consistent recovery and a lesser relapse than G4.18 alone. Treatment controls course was identical to unreacted controls.

DETAILED DESCRIPTION OF THE INVENTION

As indicated above, the present invention relates to the induction of immune tolerance in a subject by inhibiting Th1 cell immune response which would otherwise have been initiated in response to exposure to allo- or xeno-antigens present on transplanted tissue or to autoantigens associated with an autoimmune disease. The invention involves administering to the patient amounts effective to induce immune tolerance by inhibiting Th1 cell immune response of an anti-CD3 monoclonal antibody and IL-5 or an analogue thereof.

By reference to the phrases "inducing immune tolerance" or "inducing graft immune tolerance" it is intended to infer that there is an incapacity caused within the subject being treated to respond to a particular alloantigen, xeno-antigen or autoantigen. At present there are difficulties associated with known assays for in vivo determining tolerance. Although not always a reliable indicator, it is possible to obtain an indication of whether tolerance has been established by conducting in vitro assays such as mixed lymphocyte cultures and cytotoxic T cell assays. Immune tolerance is of course to be contrasted with immunosuppression which may be achieved in transplant patients as a result of administration of immunosuppressive drugs such as corticosteroids, cyclosporin and rapamycin. In fact there are reports that immunosuppressive drugs such as those mentioned may block induction of tolerance and allow rejection of allografts.

In the case of tolerance induction the recipient of an allo or xenograft the desired outcome of course is that the original graft is accepted without the requirement for long term immunosuppression. Tolerance is demonstrated if there is acceptance of a second graft from the same donor while maintaining the ability to reject grafts from genetically unrelated individuals. In human patients it may, for obvious reasons, be difficult to confirm tolerance by these means. It is generally possible to use in vitro assays, such as those referred to above. In such assays T cells taken from the recipient will not respond to donor antigens in vitro where tolerance has been induced within the recipient. The standard in vitro assay adopted is the mixed lymphocyte culture where in the case of tolerance the proliferation of host T cells is substantially absent in response to specific donor antigens, but where response to third party antigens remains normal. In the cytotoxic T cell assay tolerance is indicated where the ability to generate cells to kill donor antigens is substantially absent but where killer cell response to third party antigens remains normal.

The form of tolerance induced by anti-CD3 mAB and IL-5 therapy appears to be unrelated to loss of allo reactivity of T cells to donor antigen, in vitro. In the case of use of methods of the present invention for induction of allotransplant tolerance, the end point achieved which can be readily detected is that the graft tissue functions normally without rejection and without the need for immunosuppressive therapy. Similarly, in the case of methods of the present invention being utilised in treatment of autoimmune disease it is not claimed that the result will be elimination of auto-reactive T cells, but rather that these will be controlled by as yet undefined regulatory cells. In this case therefore success of treatment of autoimmune disease by methods of the invention can be confirmed by reduction in progression of the disease including reduced relapse rates and cure from disease symptoms.

Without wishing to be bound by theory, it appears most likely to the present inventors that a mechanism involved is that regulatory T cells, especially $CD4^+CD25^+$ T cells are induced.

The present inventors believe that the methods according to the present invention are effective as a result of inhibition of Th1 cell response. In this way release of Th1 cytokines will be substantially eliminated. This can readily be determined by RT-PCR analysis for concentrations of Th1 cytokine mRNA extracted from grafted tissue or an autoimmune diseased organ or from a lymph node draining therefrom. Therefore, as outlined above, given that Th1 cells are responsible for release of IL-2, IFN-γ and TNF-β it would be expected in a patient where Th1 immune response is inhibited for the concentrations of these cytokines to be reduced relative to levels in a syngeneic graft or in the subject's own tissue. It is also possible to detect inhibition of Th1 cells by detecting reduction of the Th1 cell marker IL-12Rβ for example by RT-PCR for IL-12Rβ mRNA.

In order to be of a clinical benefit it will be necessary for an effective amount for inhibiting Th1 immune response or for inducing graft transplant or autoimmune tolerance of anti-CD3 monoclonal antibody and IL-5 or an analogue of it to be administered. Appropriate dosage levels would be readily apparent to a trained physician, taking into account the disorder the patient is suffering from and the patient's general state of health as well as the patient's height, weight, sex along with knowledge of other prescribed medication. For example, it may be appropriate to administer a dose in the range of between 500,000 to 25,000,000 units per day of IL-5, its analogue or mimetic, with the likelihood that a high dose that saturates the relevant receptor will be required to produce the desired clinical effects. In this context the term "units" is based upon the dilution of cytokine that is required for 50% of maximum proliferation of B13 cells, as described in reference 17. For example, a dose of between 2,000,000 to 8,000,000 units, preferably approximately 4,000,000 units per day, may be appropriate.

In the case of anti-CD3 monoclonal antibodies, a dose of in the order of 1 mg to 50 mg twice daily, daily, every second day, twice weekly, or weekly may be appropriate, for example.

In a preferred dosing regime IL-5, its analogue or mimetic may, for example, be administered twice daily, daily, every second day, twice weekly or weekly for a period of between several days to several months after an allo or xenotransplant or as a treatment of autoimmune disease. Preferably, IL-5 may be administered once daily for a period of two to four weeks in order to achieve the desired clinical effect. A similar dosage regime is envisaged for anti-CD3 monoclonal antibody administration.

Particularly for use in human patients, the anti-CD3 monoclonal antibodies according to the invention will preferably be humanised. Preferably, in order that the anti-CD3 monoclonal antibody does not activate T cells it will lack an Fc that binds to Fc receptors of the subject. In the case of a human subject therefore the monoclonal antibody will lack an Fc that binds to human Fc receptors. There are a number of suitable anti-CD3 monoclonal antibodies commercially available, such as for example ORTHOCLONE™ commercially available from Ortho Pharmaceuticals, Raritan, N.J., United States of America. Preparation of humanised anti-CD3 monoclonal antibodies is also described in references 40 to 43, the disclosure of which are included herein in their entirety by way of reference. Suitable monoclonal antibodies may also be prepared according to the methods as for example described in WO 91/01752, WO 93/19196, GB 2,268,744, WO 98/39363, WO 96/32137 and U.S. Pat. No. 5,885,573 in conjunction with routine techniques well known to persons skilled in the art as outlined in current protocols in molecular biology by Ausubel, F. M., et al (1987), Wiley Interscience (ISBN 047150338), the disclosure of which is included herein in its entirety by way of reference.

The IL-5 utilised according to the present invention may be extracted and purified from natural sources. More preferably, however, the IL-5 utilised may be recombinantly produced by cloning and transfecting into a suitable cell line a nucleotide sequence encoding for IL-5 or an analogue thereof, utilising an appropriate vector and according to methods well known in the art, as for example described in reference 11 and with reference to techniques outlined in Ausubel et al, as referred to above. Although it is preferred that the IL-5 utilised will be identical to that endogenous within the species of the subject under treatment, it is nonetheless possible to use IL-5 molecules derived from any of a variety of species, for example rat, mouse, cattle, or primate. It is of course preferred that human IL-5. should be utilised in the case of treatment of a human subject.

It is additionally possible for analogues of IL-5 which, relative to the amino-acid sequence of an endogenous IL-5, have a sequence with single or multiple amino acid substitutions, deletions and/or transpositions, as long as the analogue adopted exhibits substantially analogous activity as endogenous IL-5.

The methods according to the present invention may, as has been indicated above, be adopted in the treatment of autoimmune diseases. The term "autoimmune disease" is intended to encompass those diseases or disorders within a human or mammal wherein antibodies or T lymphocytes are reactive with antigenic determinants of the human or mammal itself. Autoimmune diseases are characterized by pathological change to cells of the organism resulting from a cell-mediated immunological response and by the release of auto-antibodies, the presence of which can be detected by routine immunoassays. Some examples of diseases considered to constitute autoimmune diseases are type 1 diabetes, multiple sclerosis, rheumatoid arthritis, asthma, psoriasis, atopic dermatitis, glomerulonephritis, myasthenia gravis, chronic inflammatory demyelinating neuropathy, inflammatory bowel disease, chronic active hepatitis, interstitial pneumonitis, dermatomyositis or systemic lupus erythematosis. This list is not intended to be exhaustive.

The subjects who may benefit by treatment according to methods of the present invention include mammals, such as laboratory animals such as rats, mice, guinea pigs and rabbits, domestic animals, such as cats and dogs, farm animals such as cattle, sheep, goats, horses, primates such as gorillas, apes, baboons, chimpanzees. In particular, the subjects treated according to methods of the invention are humans.

The methods according to the present invention can effectively be utilised to induce tolerance to transplanted tissue, and thereby prevent transplant tissue rejection. In this case the transplanted tissue may constitute an allotransplant, that is a tissue derived from another member of the same species, or a xenotransplant which is a tissue derived from a member of another species. For example, given the significant shortage of human transplant tissues available and the difficulties associated with matching transplant tissues with patients having corresponding or acceptable blood or tissue type, significant research has been conducted into xenotransplantation. It is believed to be possible to genetically modify an animal from another species which has organs or tissues compatible with those of the donor species such that the transplant organs express antigenic determinants or surface proteins compatible with those of the recipient species. In this way it may be possible to avoid the initiation of cross species immune reactivity when tissues or organs are xenotransplanted. Xenotransplantation of pig organs into humans is mentioned as a specific example given the approximate size compatibility of pigs and humans and the similarity of many pig and human tissues/organs.

It is also mentioned by way of example that tissue allo or xenotransplanted to a subject in need of a transplant may constitute kidney, liver, heart, lung, skin, pancreas, lens, cornea, bone marrow, muscle, connective tissue, vascular tissue, gastrointestinal tissue, nervous tissue or bone. It may be the case that whole organs or small sections of organ tissue are transplanted, naturally according to procedures well established by the surgical profession.

According to another aspect of the invention there are provided pharmaceutical and veterinary compositions that include anti-CD3 monoclonal antibodies and IL-5 or an analogue thereof. Such compositions would generally also include one or more suitable pharmaceutical carriers and/or excipients, such as for example those disclosed within Remmington's Pharmaceutical Sciences, Mack Publishing Co., Easton, USA, 18th Edition, 1990, the disclosure of which is included herein in its entirety by way of example. In a preferred form of the invention the compositions will be in the form of injectable compositions for parenteral injection. For example, the compositions may be administered by intravenous, intramuscular, intraperitoneal or subcutaneous injection or alternatively, by direct injection into an organ. It is also possible for compositions according to the invention which comprise either one or both of the active ingredients to be enterically coated, as well understood in the art, and administered orally.

Compositions according to the present invention can be prepared by simple admixture of the active ingredients with the suitable carrier and/or excipients.

Another aspect of the invention relates to kits which can be utilised in methods according to the invention. For example, kits according to the invention may include separate vials or containers of an anti-CD3 monoclonal antibody and IL-5 or an analogue thereof, with the intention that these components are to be administered simultaneously or consecutively to a subject requiring treatment.

The present invention will now be further described with reference to the following examples:

Example 1

Experimental Materials and Methods

Cloning of rat IL-5

Rat IL-5 was cloned and transfected into CHO-K1 cells, as described (11). IL-5 transfected CHO-K1 cells were cultured in DMEM-F12 medium (Gibco BRL), 10% FCS and a selection marker Hygromycin (Boehringer Mannheim, Mannheim, Germany). rIL-5 was collected as serum free cell culture supernatant and purified by the Flag fusion system (Scientific Imaging Systems, New Haven, Conn.). The purified rIL-5 was filtered (0.2 µm), aliquoted and stored at −70° C. rIL-5's biological activity was confirmed in vitro by its ability to support growth of B13 cells (Dr C Sanderson, Perth, Wash., Australia) as described (17). One unit was defined as the dilution required for 50% of maximum proliferation. Preparations had 0–<0.06 EU/ml of endotoxin (Limulus Amebocyte Lysate assay, Coatest Gel-LAL, Chromogenix AB, Moindal, Sweden).

Other Cytokines and Monoclonal Antibodies

Human rIL-2 (Boehringer Mannheim) was administered at 20,000 units per day for 10 days, a dose that breaks induction of transplantation tolerance in rats (27). rIL-4 transfected CHO-K1 cells (Dr. D. Mason, Oxford, UK) were used to produce rIL-4 (16) and one unit was defined as the dilution that gave 50% of maximal class II MHC expression on B cells. 20,000 units per day for 10 days prolongs neonatal allograft survival in rats (9). As a control, supernatant from non-transfected CHO-K1 cells was concentrated as per cytokines.

Mouse clones used to produce mAb as described (15), were TRFK5 (IgG1) anti-human IL-5 (Dr W. Sewell, Centre for Immunology, Darlinghurst, Australia); MRC OX38 (IgG1), anti-rat CD4 (Dr. D. Mason); G4.18 (IgG3), anti-CD3 (24); as well as A6 (IgG1) and BCLA-8 (IgG3) (Dr. N. Pearce, Centenary Institute, Sydney, Australia) isotype controls with no reactivity to rat. mAb was given i.p. on day of and days 3, 7, 10 post transplant at 3.5 mg/kg body weight for MRC OX38, and 7 mg/kg for G4.18, TR FK5, MRC OX81, A6 and BCLA-8. The effects of MRC OX38 (15) and G4.18 (17, 28, 12) therapy on DA and Lewis rats have been described. Ten days after a single dose of MRC OX81, 1 ml of sera from DA rats blocked 40,000 units of IL-4 (16).

Animals and Heart Transplantation

DA (RT1$^a$), PVG (RT1$^c$), and Lewis (RT1$^l$) rats were bred and maintained at the Animal House, Liverpool Hospital. All experiments had approval from the Ethics Committee of the University of NSW. The methods of neonatal and adult heart grafting were as described (9, 16). Experimental groups with a minimum of six age and sex matched rats were treated with rIL-5 (4,000 units/rat/day) or other cytokines from the day of grafting until day 10 post transplantation. Sera was taken at day 14 to determine the alloantibody response, including IgG, IgG1, IgG2a, IgG2b and IgM isotype, as described (9). Three animals in each group were sacrificed at 10 days with tissue taken for analysis of cytokine mRNA using RT PCR.

RNA Extraction and Reverse Transcription (RT) PCR

Semi-quantitative RT-PCR technique and the sequences of oligonucleotide primer pairs for IL-2, IL-4, IL-5, IL-10, IFN-γ and GAPDH were as described (15). Primers for IL-12 p35 were 5' tgt gtc aat cac gct ace tcc tc; 3' gtg gaa gaa gtc tct eta gta gc, for IL-12 p40 were 5' ctg ccc aac tgc cga gga gac c, 3' gga atg ggg agt gct cca gga (NCBI Ac No U16674); and for IL-12 β receptor were 5' cct ata tct gtt atg aaa tca gg, 3' ctg tea cag ctg tca tcc ata. GAPDH was used as a positive control to confirm there were equivalent cDNA levels in all samples.

Multiple RT-PCR reactions were performed on each sample and duplicate tubes were removed, within the linear phase of amplification, at three cycles intervals for IL-2 and IL-4 and five cycles intervals for all other cytokines. A dilution series of cDNA from ConA stimulated lymphocytes was analyzed for each primer set and showed that 5-10 fold differences in mRNA levels were detected for all cytokines (15) (smaller differences were not considered biologically relevant). Analysis of samples from separate experiments, with 4-6 animals for each treatment group, allowed demonstration of any consistent result.

Statistical Analysis

Graft survival times and results of cytokine quantitation by RT-PCR in different treatment groups were compared using Peto-Wilcoxon Rank Test and $p<0.05$ was considered a significant difference.

Example 2

Effect of IL-5 on Allograft Rejection

To examine the effects of IL-5 therapy on allograft responses DA rats were given 4000 units of recombinant rat IL-5 (rIL-5) by intra-peritoneal injection daily for 10 days, commencing on the day of transplantation of fully allogeneic PVG neonatal cardiac allografts. This treatment delayed rejection to 27 (23-47) days (median (range)), compared to normal rejection in untreated controls at 14 (10-14) days ($p<0.001$) and to controls treated with supernatant from non-transfected CHO-K1 cells 13 (10-15) days ($p<0.001$) (FIG. 1). This experiment was repeated five times with a similar significant delay in rejection. The combined results were 26 (16-49) (n=23) for rIL-5 treated compared to untreated controls 13.5 (10-15)(n=20)($p<0.0001$). A ten-fold increase in dose of rIL-5 (40,000 units per day) had a similar effect, but a lower dose of 400 units per day did not delay rejection.

Co-administration of IL-5 with a monoclonal antibody (mAb) that blocks function of IL-5 (TRKF5) (FIG. 1a) resulted in rejection in a similar tempo to untreated controls of 14.5 (14-17) days (n=6). Controls treated with TRKF5 alone (FIG. 1) or isotype control mAb (A6) also rejected in normal tempo. Co-administration of A6 did not affect the ability of rIL-5 to delay rejection (data not shown). Ten days after a single dose of TRKF5 each ml of sera could block 15,000 units of rIL-5 (FIG. 1a). The peripheral blood eosinophil count rose in rIL-5 (1.5±0.94%) and rIL-51A6 treated (1.4±0.42%) compared to rIL-5/TRKF5 treated (0.9±0.39%) and untreated controls (0.7±0.17%)($p<0.03$). rIL-5 had no effect on other peripheral blood leukocyte counts. These studies demonstrated rIL-5 delayed fully allogeneic neonatal cardiac allograft rejection, and that the effect was specific to rIL-5 as co-administration of a blocking mAb prevented prolongation of graft survival and eosinophilia.

Example 3

Effect of IL-5 on Induction of Tolerance

Figure 2:
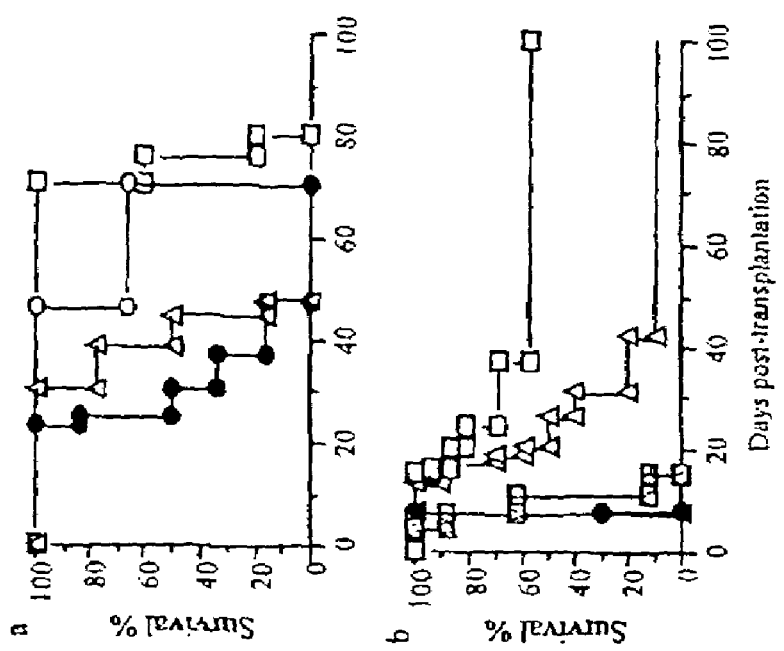

To examine whether rIL-5 could enhance induction of tolerance to an allograft, this therapy was combined with anti-T cell mAb therapies that if given alone only serves to delay rejection. Anti-CD4 (MRC 0x38) mAb given to DA rats with PVG neonatal heart grafts delayed rejection to 25-44 days (FIG. 2a), and when combined with rIL-5 all the grafts survived over 70 days ($p<0.01$). In this model the small pieces of neonatal heart do not function indefinitely (29) as syngeneic grafts fail due to non-immunological causes between 50 and 100 days (FIG. 2a).

The effect of rIL-5 in a heterotopic adult heart graft model was also examined, as indefinite graft survival can be induced without non-immunological graft loss. rIL-5 therapy alone had no effect on PVG adult allograft survival in "low responder" DA rats. As anti-T cell mAb therapy alone readily induces tolerance in the low responder DA model, we examined if rIL-5 could facilitate induction of tolerance in the "high responder" Lewis strain. In these rats anti-T cell mAb alone only delays rejection (12), and long term graft acceptance is rarely obtained without high dose combinations of immunosuppressive therapies (12, 25). Anti-CD3 mAb (G4.18) therapy delayed rejection from 7 (7-8) days in untreated controls to 23 (13->100) days and only one of 16 rats accepted their grafts long term (>100 days) (FIG. 2b). rIL-5 therapy alone did not delay rejection in this model, but when combined with G4.18 therapy it further prolonged graft survival ($p<0.028$) than with G4.18 therapy alone. Nine of sixteen rats with combined anti-CD3 and IL-5 accepted their grafts >100 days. These rats, with long surviving grafts, accepted a second donor strain PVG skin graft but rejected a third party graft, consistent with tolerance induction. In control experiments Lewis recipients treated with G4.18 and rejected faster than with G4.18 alone. Combined anti-CD3 mAb and CHO-K1 supernatant had rejected in a similar time to those treated with anti-CD3 alone. rIL-4 or CHO-K1 supernatant therapy alone also had no effect on graft survival. These studies demonstrate that rIL-5 facilitated induction of tolerance when combined with anti-CD3 cell mAb that alone can only delay graft rejection.

Example 4

Mechanism of Action of rIL5 on Alloimmune Responses

Figure 3:
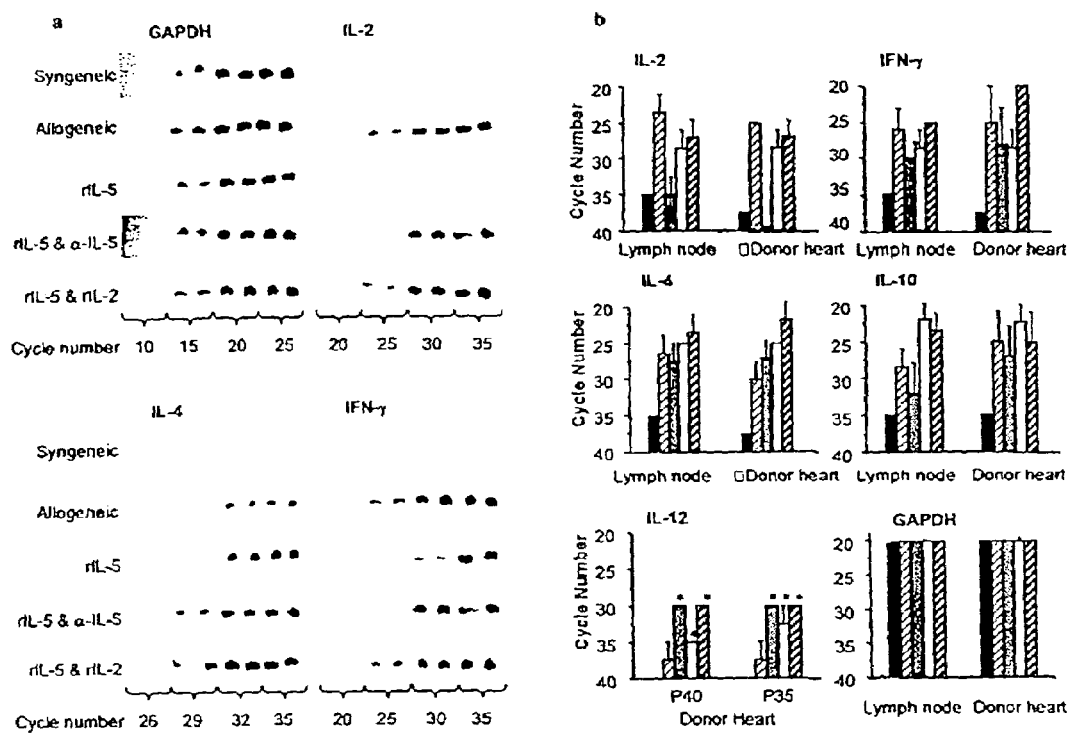

To examine the mechanisms of action of rIL-5 on alloimmune responses, concentrations of mRNA for Th1 and Th2 cytokines in the neonatal heart allografts and draining lymph node were determined by RT-PCR (FIG. 3). Untreated controls had significantly higher levels of IL-2, IFN-γ, IL-12p35, IL-12p40, IL-4 and IL-10 mRNA compared to syngeneic grafts and the recipient's own heart, which indicated the expression was due to the infiltrate related to the allograft response (9). IL-2 mRNA levels were less in rIL-5 treated groups, both in the heart allografts (p<0.001) and in the regional nodes (p<0.0001), compared to untreated controls or rats treated with both rIL-5 and TRFK5. After rIL-5 treatment there was less IFN-γ mRNA in lymph node (p<0.01), but not in donor heart. IL-12 p35 and p40 mRNA levels were increased in all rIL-5 treated groups compared to rats with normal rejection. The Th1 cell marker IL-12Rβ was not detected in rIL-5 treated heart grafts but significant levels were detected in controls. mRNA levels of the Th2 cytokines 1'-4 and IL-10, were similar in rIL-5 and untreated control rats.

The methods of semi-quantitative RT-PCR of cytokines including primers have been described (23). Primers were designed from published mice/human sequences using areas of high homology and included IL-12 p35 (5' tgt gtc aat cac get ace tee tc; 3' gtg gaa gaa gtc tct eta gta gc), IL-12 p40 (5' ctg ccc aac tgc cga gga gac c, 3' gga atg ggg agt get cca gga) (NCBI Ac No U16674), IL-12 b receptor (5' cct ata tct gtt atg aaa tca gg, 3' ctg tea cag ctg tca tcc ata).

Example 5

Role of IL-2 or IL-4 in IL-5 Effect on Alloimmune Response

Figure 4:
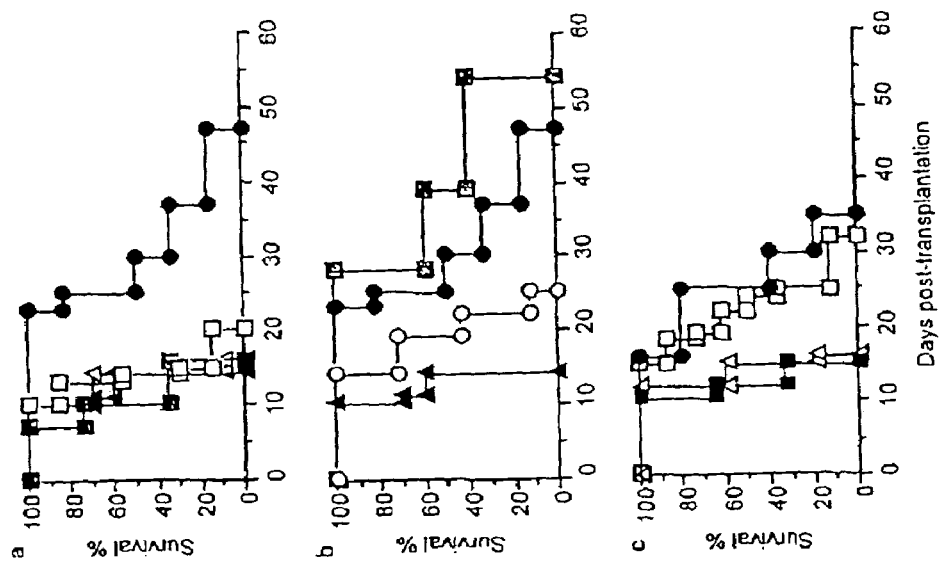

To examine if lack of IL-2 contributed to the delayed graft rejection with rIL-5 treatment, the effects of co-administering rIL-2 and rIL-5 were examined (FIG. 4a). rIL-2 treatment abolished the ability of rIL-5 to prolong graft survival, 14 (10-20) days. This was associated with induction of mRNA for IL-2 and IFNγ in the hearts and regional nodes to levels similar to normal rejection (FIG. 3). We have previously described that rIL-4 treatment also delays graft rejection and can facilitate induction of tolerance with anti-CD4 mAb therapy (9). This therapy induces mRNA for Th2 (IL-4, IL-5), and does not inhibit Th1 (IL-2, IFN-γ) cytokines. To examine whether rIL-4 could facilitate induction of tolerance by rIL-5, these therapies were combined. Paradoxically, rejection occurred earlier than with either rIL-5 or rIL-4 alone (FIG. 4b). Blocking endogenous IL-4 with MRC 0×81 mAb did not prevent the prolongation of graft survival by rIL-5 (FIG. 4c).

Example 6

Expression of IL-5 Alpha Chain Receptor

The expression of IL-5 alpha-chain receptor was examined by RT-PCR of mRNA from tissues and cells; lymph node and spleen cells from normal tissue had no receptor. Enriched T cell and bone marrow cells had no receptor, while B cells had receptor. There was also no receptor mRNA isolated from dendritic cell cultures, prepared from DA rat bone marrow cells cultured in RPMI with a mixture of 10% fetal calf serum and 5% rat serum with GM-CSF (800 units/ml) (R&D Systems Inc. USA), rat IL-4 (400 units/ml) and rat TNF-α (10 ng/ml) (R&D Systems Inc., Minneapolis, USA) for 10 days. Cell cultures had 40% MRC 0×62+ cells (dendritic cells) and 35% ED1+ cell (macrophages) as stained with an indirect immunoperoxidase technique, described (23). The effect of rIL-5 on cultured dendritic cells was examined. Dentritic cell enriched cultures when exposed to rIL-5 did not alter their expression of Th1 dendritic cell cytokines, including IL-6, IL-12 p35, IL-12 p40 and TNF-α. When bone marrow cells were exposed to rIL-5 from the commencement of culture with GM CSF, IL-4 and TNF-γ there was no inhibition of the development of MRC 0×62 and ED1 cells, but these cells had no detectable mRNA for Th1 dendritic cell cytokines, including no IL-12 p35, IL-12 p40, IL-6 and TNF-γ nor of the IL-12 receptor beta 2 chain which is expressed by Th1 dendritic cells. Blocking the effects of rIL-5 with the mAb TRKF5 allowed expression of these Th1 dendritic cell markers. Thus the rIL-5 has an effect on these cells even though they do not express the IL-5 alpha chain receptor. This is possibly by IL-5 ability to bind to the shared GM-CSF, IL-3, IL-5 receptor beta chain, where it may have blocked full activation of Th1 dendritic cells, and diverted the dendritic cell maturation to a Th2 or Tr1 stimulating phenotype.

Conclusions

The studies reported in Examples 1 to 6 demonstrate that IL-5 acts as an immunoregulatory cytokine that can contribute to the induction of tolerance to allografts. IL-5 binds to receptors composed of an IL-5 specific alpha chain and a beta chain shared with the IL-3 and GM-CSF receptor (10). In man and mice, the IL-5 receptor alpha chain is restricted in its expression to eosinophils, basophils and some activated B cells (10). We confirmed this restricted expression in rats (data not shown). Increased IgG1 alloantibody was observed in rIL-5 treated rats consistent with rIL-5 promoting isotype switching in B cells. As anti-CD4 mAb therapy, when combined with rIL-5, blocked alloantibody production and further prolonged graft survival, it is unlikely that alloantibody mediating enhancement was the mechanism by which graft survival was prolonged. It is possible that eosinophils and basophils activated by rIL-5 inhibit rejection by yet to be defined mechanisms. rIL-5 can also activate preformed GM-CSF receptors which are present on a wider variety of cells than the specific IL-5 receptor (20). Consistent with rIL-5 acting on cells not expressing IL-5 receptors, we have shown that rIL-5 interfered with GM-CSF induced growth of dendritic cells in vitro. The precise mechanism of action of IL-5 in the allograft response is being investigated further.

The $CD4^+CD25^+$ regulatory cells that maintain tolerance to transplanted tissues (30, 16) may function by the release of multiple cytokines including IL-5, that act synergistically. Th2 cells, which produce IL-5 as well as IL-4 and IL-10 have been extensively investigated as mediators of tolerance because of their ability to down-regulate Th1 cells. IL-4 and IL-10 have paradoxical effects on allograft survival, in that they can accelerate (31, 32) or delay (9, 33, 34) graft rejection. This paradoxical effect of IL-4 was also demonstrated in our studies. rIL-4 did not facilitate induction of tolerance with rIL-5 or ant-CD3 mAb therapy but did with anti-CD4 (9). With anti-CD4 therapy in DA rats with PVG allografts, Th2 cells were preferentially blocked and Th1 cells spared (15). With anti-CD3 or rIL-5 therapy, Th1 cells are inhibited and Th2 cells are spared (17). It is possible that in situations with a dominant Th2 response, IL-4 promotes generation of Th2 cells that reject the graft (35), whereas in situations where Th2 cells are inhibited the dominant effect of IL-4 may be to inhibit Th1 cell activation, thus allowing tolerance induction. Tr1 cells which produce IL-5, IL-10 and TGF-β and small amounts of IL-2 (but not IL-4) can regulate Th1 mediated auto-immune colitis (8) and immune mediated diabetes (36). Previous studies on Tr1 cells have focussed on the effects of IL-10 and TGF-β but have not proposed a role for 1'-5. Our studies suggest IL-5 is an important partner cytokine in both Th2 and Tr1 cells function. This cytokine, which to date has been thought of as a mediator of allergic reactions, is also be a key regulator that inhibits Th1 responses when used in conjunction with anti-CD3 antibodies.

Example 7

IL-5 and Anti-CD3 Synergy in Model of Nephritis Autoimmune Disease

Figure 5:
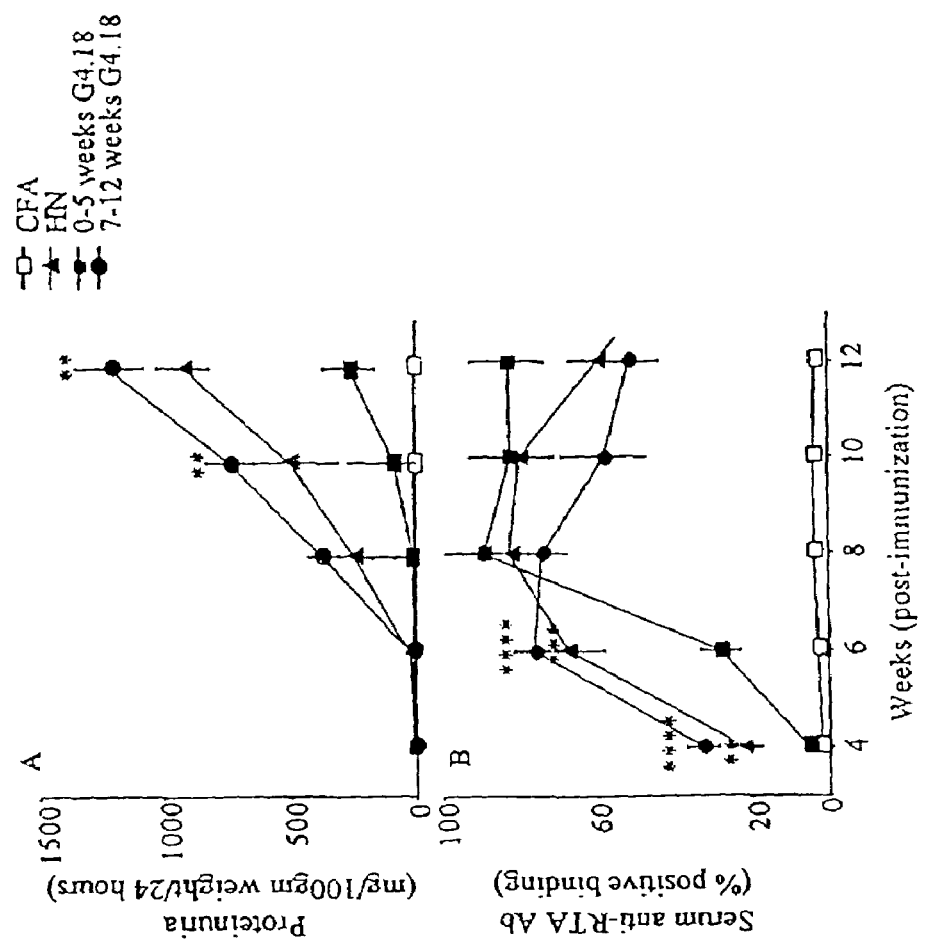
Figure 6:
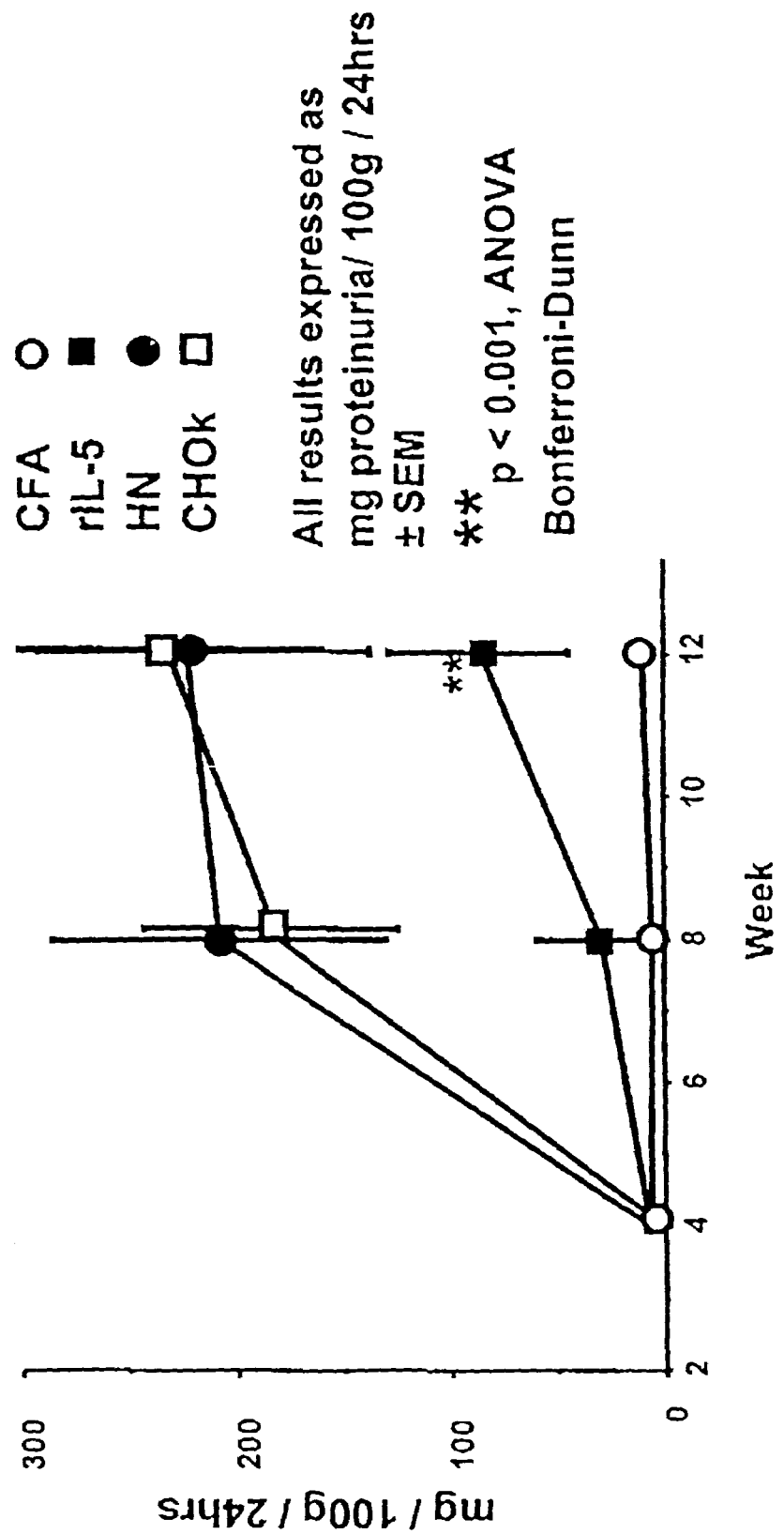

We have demonstrated that active Heymann nephritis, the model of human membranous glomerulonephritis is mediated by $CD8^+$ T cells injuring the glomerulus 6-8 weeks after immunized with antigen. These T cells develop in response to antibody and complement depositing in the glomeruli. They represent a second response to the initial immune insult. We have examined the effects of a variety of therapies on the development of glomerulonephritis. At the time of immunization many therapies work, including cyclosporine, mycophenolate mofetil, anti-CD4 and anti-CD3 monoclonal antibody therapy. However, if therapy is delayed to 4-6 weeks after immunosuppression, most of these therapies (including cyclosporine, mycophenolate mofetil, and anti-CD4 monoclonal antibodies) do not work. However total depletion of $CD8^+$ T cells by thymectomy and anti-CD8 monoclonal therapy does block proteinuria, by depleting $CD8^+$ cytotoxic T cells. We have extended this work to demonstrate that anti-CD3 mAb therapy (G4.18) does also partially block disease onset, it does so by inhibiting Th1 $CD8^+$ cytotoxic T cell function (FIG. 5). Further we have recently demonstrated that rIL-5 therapy has a similar effect to anti-CD3 monoclonal anti-body therapy (FIG. 6). A similar effect has also been demonstrated with rIL-4 therapy, and synergy with anti-CD3 monoclonal antibody therapy has been demonstrated. Controls given CHO-K1 supernatant or the cytokine rIL-13, which has similar effects to IL-4 on macrophage function, has no effect. These studies demonstrated that a $CD8^+$ Th1 mediated autoimmune disease can be inhibited by administration of anti-CD3 monoclonal antibody and rIL-5 therapy, consistent with our findings in transplantation.

Example 8

We have demonstrated that anti-CD3 monoclonal antibody therapy has a dramatic effect in reversing symptoms in two models in which there is demyelination induced by immunization with antigens present in nerve cells. In experimental allergic encephalomyelitis (EAE) we have demonstrated that treatment of rats that have just become paralysed leads to an immediate arrest of the disease and a recovery to normal within 48 hours. This is 4-6 days faster than with no treatment or control treatment. rIL-5 in isolation had no effect, but there appeared to be a slightly faster and more complete recovery when cytokine was combined with anti-CD3 monoclonal antibody therapy. This will be confirmed in further studies. Unfortunately, the dramatic recovery associated with anti-CD3 monoclonal antibody alone was followed by a relapse that is more severe than if animals had been allowed to recover without therapy. This relapse is presumed to be due to the fact the anti-CD3 monoclonal antibody induces anti-idiotypic antibodies that block its function within 7-8 days. After this the effector Th1 cells can mediate a relapse. Further it may have impaired the generation of regulatory cells to can restore tolerance. In fact rats with normal EAE are resistant to re-induction of disease by re-immunization with myelin basic protein in adjuvant. The relapse after anti-CD3 therapy was partially eliminated by co-administration of rIL-5. Thus the combination therapy led to re-establishment of tolerance.

IL5 and Anti-CD3 Synergy in Models of Demyelination Autoimmune Disease

Figure 7:
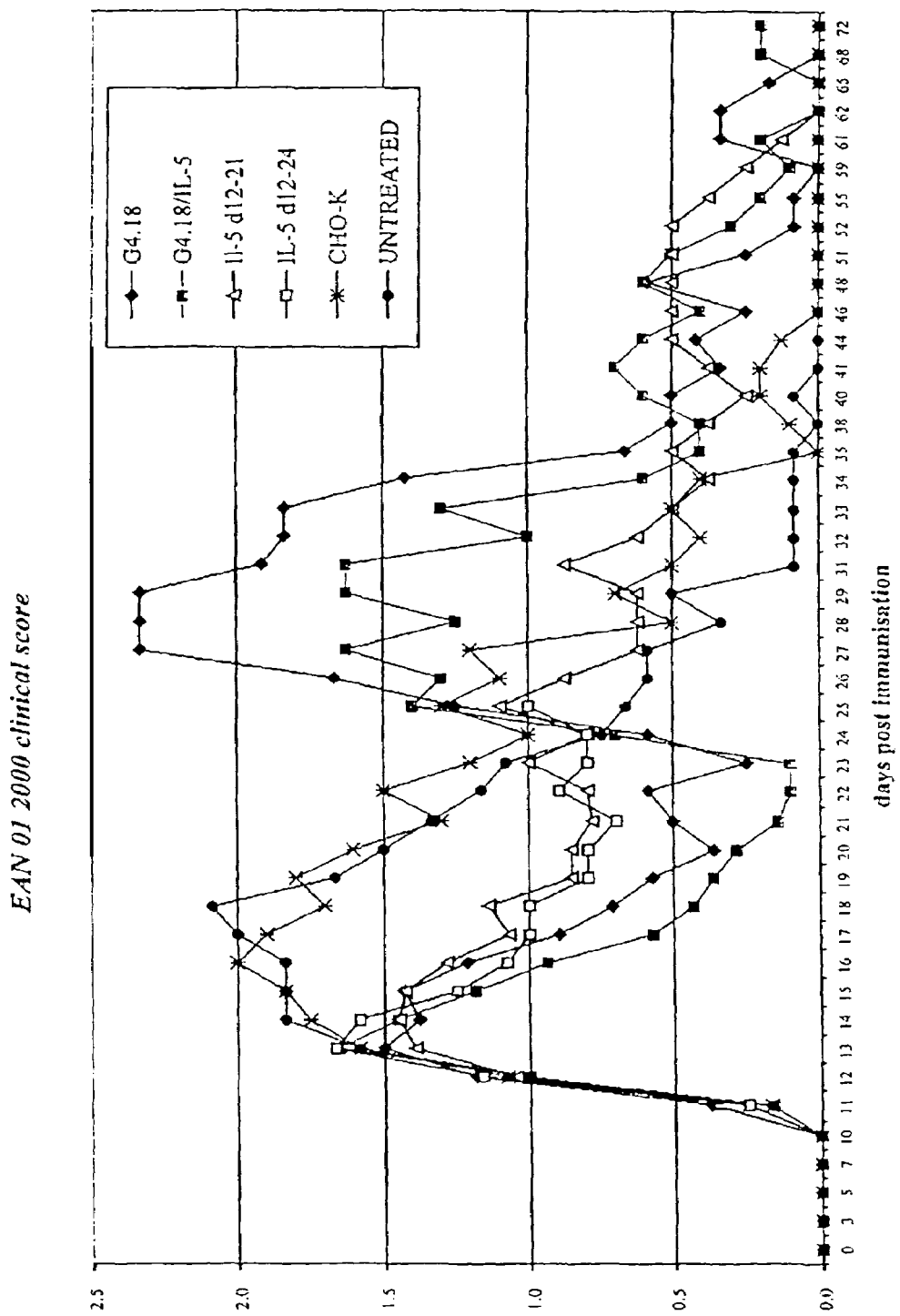

In a second model of demyelinating disease known as experimental allergic neuritis (EAN), rats develop injury to their peripheral nerves after immunization with bovine nerve root myelin. In EAN, treatment of Lewis rats with anti-CD3 monoclonal antibodies from the day of onset of symptoms leads to more rapid recovery of paralysis (FIG. 7). Again the rats relapse more severely than if the disease had recovered according to its natural course. Although rIL-5 therapy had a minor recovery effect on EAN, combination treatment of anti-CD3 monoclonal antibody with rIL-5 lead to a more rapid recovery than monoclonal or cytokine treatment alone and in this instance there was no spontaneous relapse. In fact the rats treated with both therapies had less relapse than untreated controls. Both EAE and EAN are mediated by $CD4^+$ Th1 cells.

Conclusions

Thus in three autoimmune disease models we have demonstrated a benefit of combined anti-CD3 monoclonal antibody therapy with rIL-5. In $CD4^+$ Th1 cell and in $CD8^+$ Tc1 cell mediated diseases, there is a beneficial effect. This is similar to allograft rejection where both $CD4^+$ Th1 cell and $CD8^+$ Tc1 cell mediate injury, and anti-CD3 monoclonal antibody combined with rIL-5 promote induction of tolerance.

Example 9

Mechanism of Action of IL-5 in Induction of Tolerance

The mechanisms by which rIL-5 works has also been a subject of investigation. rIL-5 has mainly been implicated as a mediator of inflammation in allergic diseases such as eczema and asthma. It is also involved in defence against parasitic diseases such as worms and schistosoma. IL-5 is mainly produced by T cells and is an essential growth factor for the activation of production and growth of eosinophils. It also activates basophils and mast cells. IL-5 can also promote B cell maturation and isotype switching to non-complement fixing IgG isotypes and to allergic response mediators IgE. IL-5 acts on cells via a receptor dimer consisting of an alpha chain that specifically binds IL-5 and a beta chain that it shares with IL-3 and GM-CSF. These latter two cytokines can stimulate growth of a variety of blood cell types, including dendritic cells and macrophages. IL-5 has no known direct effect on T cell, which do not express the IL-5 receptor-alpha chain. The T cell subtypes that produce IL-5 have been strongly implicated as regulators of Th1 mediated responses mediating auto-immune diseases and transplantation rejection. These include Th2 cells which produce; IL-4, IL-5, IL-6, IL-10 and IL-13 but not the Th1 cytokines IL-2, IFN-γ, TNF-β. With respect to Th2 cells IL-4 and IL-10 have been demonstrated to be the main regulators of Th1 responses by their effect on antigen presenting cells. IL-13 inhibits macrophage activation but has no effect on T cell responses.

The other major regulatory cell is the Tr1 cell that produces large quantities of IL-5, IL-10 and TGF-β. Tr1 cells also can produce some IL-2 and IFN-γ but no IL-4. Tr1 cells main action has been attributed to IL-10 and TGF-β not to IL-5. A third regulatory cell is the Th3 cell that is induced by feeding rodents auto-antigen prior to challenge with this antigen in adjuvant, eg myelin basic protein in EAE. This cell transfers tolerance and its action has been related to production of TGF-β.

Functional transfer of tolerance by $CD4^+$ T cells has been demonstrated with two cell types that are characterized by cell surface markers. L-selectin expressing cells in thymus and peripheral lymphoid tissue, and can protect against Th1 mediated thyroiditis and type I diabetes induced in lightly irradiated rats. There effects are attributed to IL-4 and TGF-β (37). The second cell expresses CD25, the IL-2 receptor-alpha chain. It can transfer transplantation tolerance and protection against autoimmune gastritis and oophoritis/orchitis induced by thymectomizing mice three days after birth (38). The cytokines involved in this cells action are not defined but do not include IL-4. Our studies on this cell suggest they are high producers of TGF-β and low producers of other cytokines (confidential unpublished information). They are however short-lived cells that require cytokines for growth and survival. Our data suggests IL-2 is not sufficient (39) and that IL-4 has the opposite effect and inhibited their survival (unpublished data. Preliminary data suggests IL-5 may promote their survival.

We have examined whether IL-5 may affect antigen presenting cells which express high levels of IL-3 and GM-CSF receptors. In these studies dendritic cells were cultured from bone marrow in the presence of GM-CSF as well as IL-4 which inhibits monocyte macrophage maturation. In these studies where rIL-5 is also added, the growth of dendritic cells is retarded and their morphology changes compared to controls. As IL-5 can bind to activated GM-CSF and IL-3 receptors we suspect this is a potential mechanism for IL-5's effect. We have shown these cultured dendritic cells do not express the IL-5 receptor alpha chain, thus their effect must be via an alternate receptor.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Dallman, M. J. & Clark, G. J. *Curr. Opin. Immunol.* 3, 729-34 (1991).
2. Cobbold, S. P., Adams, E., Marshall, S. E., Davies, J. D. & Waldmann, H. *Immunol. Rev.* 149, 1-29. (1996).
3. Nickerson, P., et al. *Curr. Opin. Immunol.* 6, 757-64 (1996).
4. Fanslow, W. C., Clifford, K. N., Parl, L. S. & et. al. *J. Immunol.* 147, 535-540. (1991).
5. Bromberg, J. S. Current Opinion Immunol. 7, 639-643 (1995).
6. Donckier, V. et al. *Transplant. Proc.* 27, 186-7 (1995).
7. Zheng, X. X., et al. *J. Immunol.* 154, 5590-600 (1995).
8. Takeuchi, T. et al. *Transplantation* 64, 152-157 (1997).
9. He, X. Y., et al. *Transplantation* 65, 1145-1152. (1998).
10. Koike, M. & Takatsu, K. *International Archives of Allergy & Immunology* 104, 1-9 (1994).
11. He, X. Y., Verma, N., Plain, K. M. & Hall, B. M. *Transplant. Proc.*, 31:1574-6 (1999).
12. Woodley, S. L., et al. *Transplantation* 56, 1443-7 (1993).
13. Trichieri, G. *Blood* 84, 4008-27 (1994).
14. Gately, M. K., et al. *Annu. Rev. Immunol.* 16, 495-521 (1998).
15. Plain. K. M., et al. *Transplantation* 64, 1559-1567. (1997).
16. Hall, B. M., Fava, L-M., Chen J., Plain, K. M., Boyd, R. A., Berger, M. F. *J. Immunol.* 161, 5147-5156 (1998).
17. Plain, K. M., et al. *Transplantation,* 67:606-13 (1999).
18. Groux, H. et al. *Nature* 389, 737-742. (1997).
19. Han, H. S., Jun, H. S., Utsugi, T. & Yoon, J. W. *J. Autoimmunity* 9, 331-340. (1996).
20. Woodcock, J. M., et al. *Blood* 15, 3005-17 (1997).
21. Macatonia, S. E., et al. *J. Immunol.* 154, 5071-5079 (1995).
22. Banchereau, J. & Steinman, R. M: *Nature* 392, 245-252 (1998).
23. Penny, M. J., Boyd, R. A. & Hall, B. M. *Kidney Int.* 51, 1059-1068 (1997).
24. Ilstand, S. T., et al *J Exp Med,* 162:231-44 (1985)
25. Ilano, A. L., et al *Transplantation,* 51:905-9 (1991)
26. Kostakis, A. J., et al *Med Sci Libr Compend,* 5:280 (1977)
27. Dallman, M. J., et al *J. Exp. Med.* 173:79-87 (1991)
28. Nicolls, M. R., et al *Transplantation,* 55:459-68 (1993)
29. Fey, T. A., et al *J. Pharmacol. Toxicol. Methods,* 39:9-17 (1998)
30. Qin, S., et al *Science* 259:974-77 (1993)
31. Nickerson, P., et al *Transplantation,* 63:489-94 (1997)
32. Qian, S., et al *Transplantation,* 62:1709-14 (1996)
33. Levy, A. E. and Alexander, J. W. *Transplantation,* 60:405-6 (1995)
34. Lowry, R. P., et al *Transplant. Proc.,* 27:392-4 (1995)
35. Picotti, J. R., et al *Transplantation,* 63:619-624 (1997)
36. Han, H. S., et al *J. Autoimmunity,* 10:299-307 (1997)
37. Seddon, B. and Mason, D. *J. Exp. Med.,* 189:279-88 (1999)
38. Sakaguchi, S., et al *Journal of Immunology,* 155:1151-64 (1995)
39. Pearce, N. W., et al *Transplantation,* 55:374-80 (1993)
40. Bolt, S., E. Routledge, I. Lloyd, L. Chatenoud, H. Pope, S. D. Gorman, M. Clark, and H. Waldmann. 1993. The generation of a humanized, non-mitogenic CD3 monoclonal antibody which retains in vitro immunosuppressive properties. *Eur. J. Immunol.* 23:403-11.
41. Xu, D., M. L. Alegre, S. S. Varga, A. L. Rothermel, A. M. Collins, V. L. Pulito, L. S. Hanna, K. P. Dolan, P. W. Parren, J. A. Bluestone, L. K. Jolliffe, and R. A. Zivin. 2000. In vitro characterization of five humanized OKT3 effector function variant antibodies. *Cellular Immunology* 200:16-26.
42. Richards, J., J. Auger, D. Peace, D. Gale, J. Michel, A. Koons, T. Haverty, R. Zivin, L. Jolliffe, and J. A. Bluestone. 1999. Phase I evaluation of humanized OKT3: toxicity and immunomodulatory effects of hOKT3 gamma4. *Cancer Research* 59:2096-101.
43. Woodle, E. S., J. A. Bluestone, R. A. Zivin, L. K. Jolliffe, J. Auger, D. Xu, and J. R. Thistlethwaite. 1998. Humanized, nonmitogenic OKT3 antibody, huOKT3 gamma (Ala-Ala): initial clinical experience. *Transplantation Proceedings* 30:1369-70.

The invention claimed is:

1. A method of inhibiting Th1 immune response in a mammalian subject suffering from an autoimmune disease, which method comprises administering to the mammalian subject effective amounts of an anti-CD3 monoclonal antibody and IL-5, or an anti-CD3 monoclonal antibody and an analogue of IL-5, wherein the autoimmune disease is selected from the group consisting of: type I diabetes, multiple sclerosis, rheumatoid arthritis, psoriasis, glomerulonephritis, myasthenia gravis, chronic inflammatory demyelinating neuropathy and inflammatory bowel disease.

2. The method according to claim 1 wherein the anti-CD3 monoclonal antibody does not bind to Fc receptors.

3. The method according to claim 1, wherein the subject is human.

4. The method according to claim 3 wherein the antibody is a humanised anti-CD3 monoclonal antibody.

5. The method according to claim 3 wherein the IL-5 is recombinant human IL-5.

\* \* \* \* \*